United States Patent [19]

Gustilo et al.

[11] Patent Number: 4,546,501

[45] Date of Patent: Oct. 15, 1985

[54] HIP PROSTHESIS

[76] Inventors: Ramon B. Gustilo; Richard F. Kyle, both of Hennepin County Medical Center - 701 Park Ave. South, Minneapolis, Minn. 55415

[21] Appl. No.: 426,092

[22] Filed: Sep. 28, 1982

[51] Int. Cl.[4] ............................................. A61F 1/04
[52] U.S. Cl. .................................... 623/23; 128/92 C; 128/92 CA; 623/22
[58] Field of Search .................. 3/1.9, 1.91, 1.911, 3/1.912, 1.913; 128/92 C, 92 CA, 92 BC

[56] References Cited

U.S. PATENT DOCUMENTS

| | | | |
|---|---|---|---|
| 3,102,536 | 9/1963 | Rose et al. | 3/1.913 |
| 3,906,550 | 9/1975 | Rostoker et al. | 3/1.913 |
| 3,965,490 | 6/1976 | Murray et al. | 3/1.913 |
| 4,135,507 | 1/1979 | Harris | 128/92 BC |
| 4,259,072 | 3/1981 | Hirabayashi | 3/1.9 |
| 4,279,042 | 7/1981 | Andriacchi et al. | 3/1.913 |
| 4,406,023 | 9/1983 | Harris . | |
| 4,435,854 | 3/1984 | Keller | 3/1.913 |

FOREIGN PATENT DOCUMENTS

| | | | |
|---|---|---|---|
| 0016480 | 8/1980 | European Pat. Off. | 3/1.913 |
| 0032165 | 7/1981 | European Pat. Off. | 3/1.913 |
| 0038902 | 11/1981 | European Pat. Off. | 3/1.913 |
| 0038908 | 11/1981 | European Pat. Off. . | |
| 2322101 | 11/1973 | Fed. Rep. of Germany | 3/1.913 |
| 560042 | 3/1975 | Switzerland | 3/1.913 |
| 1126961 | 9/1968 | United Kingdom . | |
| 1285460 | 8/1972 | United Kingdom | 3/1.913 |
| 1554454 | 10/1979 | United Kingdom | 3/1.913 |
| 2069340 | 8/1981 | United Kingdom | 3/1.913 |

OTHER PUBLICATIONS

Advertisement—Bard Contour Link SP-Prosthesis, Waldemar Link GmbH & Co.
Advertisement—Isoelastic Femoral Prosthesis Butel.

*Primary Examiner*—Richard J. Apley
*Assistant Examiner*—David J. Isabella
*Attorney, Agent, or Firm*—Sherman & Shalloway

[57] ABSTRACT

A femoral insert combines bone ingrowth surfaces in the proximal portion of the shaft which is wide in the medial-lateral direction and curved in the medial aspect with a distal portion which has a round cross-section and is curved in the direction of the anterior bow of the femur. Accordingly, firm fixation of the implant is initially provided by the distal portion functioning as an intramedullary rod while long term stabilization is achieved proximally through bone ingrowth. Also, the neck connecting the spherical head to the shaft through the collar is anteverted with respect to the collar at an angle of about 10° to 12°. The prosthesis for the left femur is basically a mirror image of the prosthesis for the right femur.

12 Claims, 12 Drawing Figures

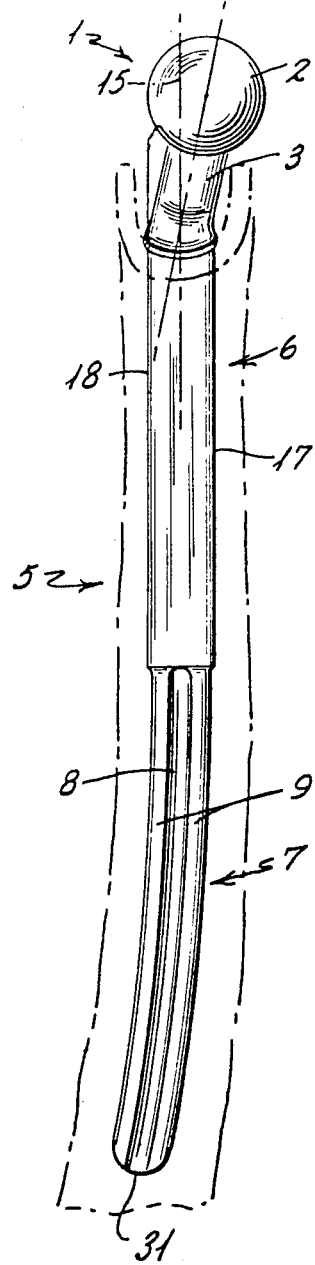
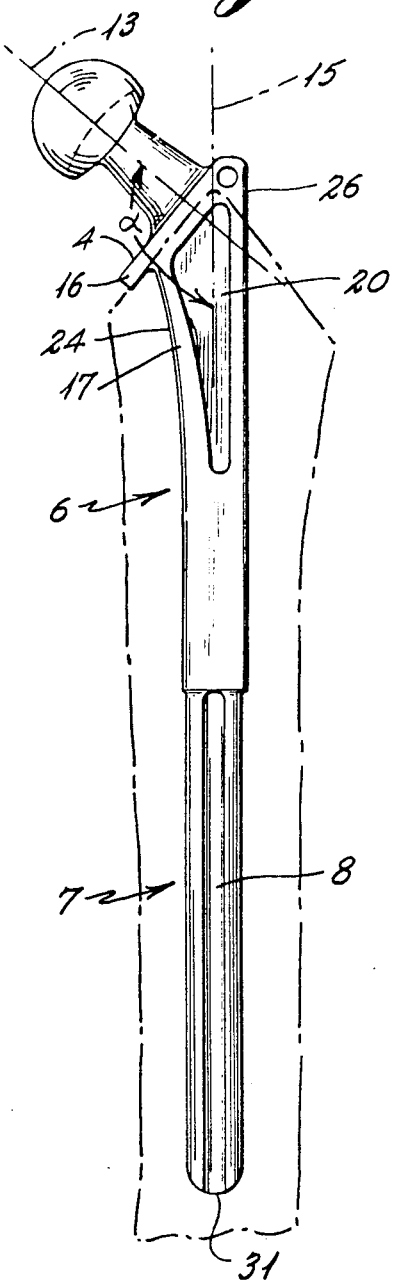
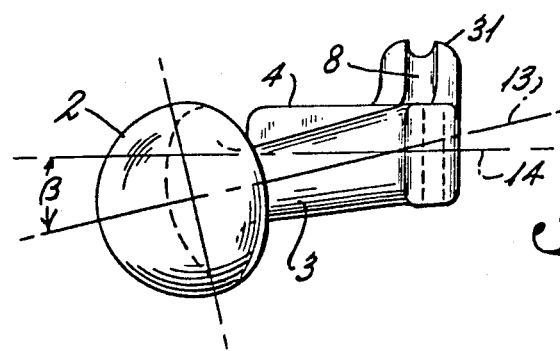

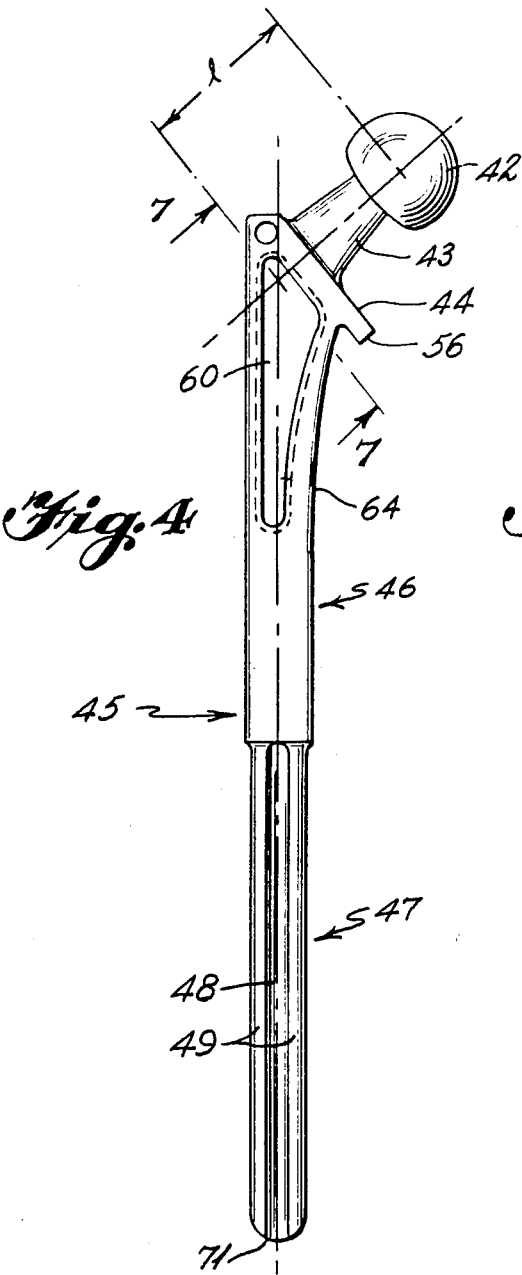
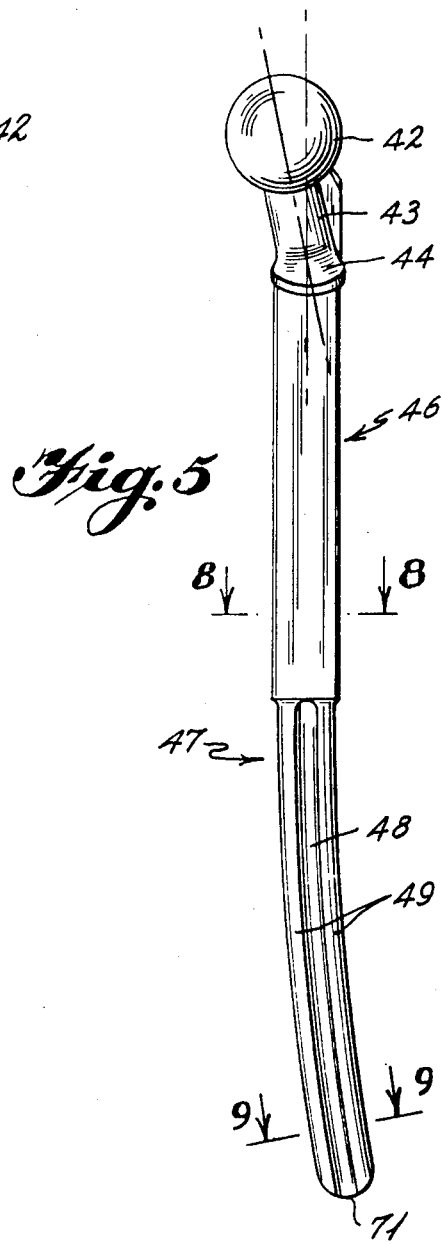
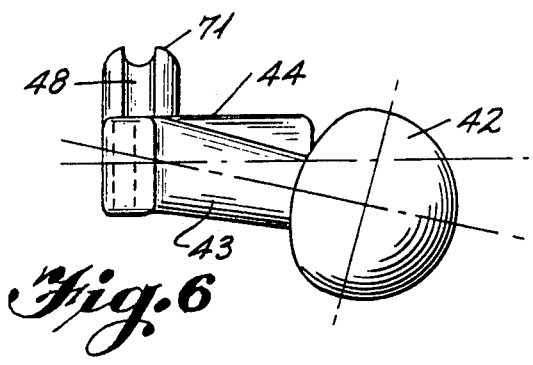

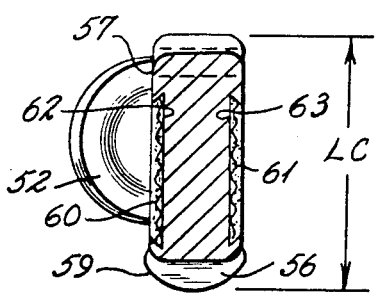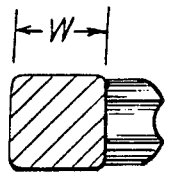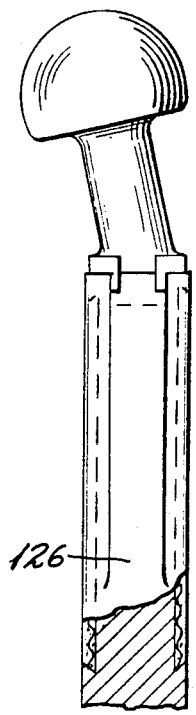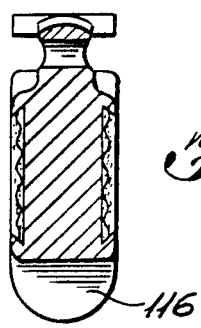

HIP PROSTHESIS

BACKGROUND OF THE INVENTION

1. Field of the Invention

This invention relates to a femur prosthetic device. More particularly, this invention relates to a hip prosthesis adapted for insertion into the upper medullary canal in the femur of a patient. The hip prosthesis of this invention is of the type generally characterized as including a head or ball member, a shaft member for insertion into the intermedullary canal, and a neck member connecting the ball and shaft or stem member, and also including at least one porous metal surface portion which provides for stablization by bone ingrowth without requiring any cement.

2. Description of the Prior Art

Hip prostheses are known in the art and these have included various design configurations of the various components, including the head member, neck, collar and shaft. Both straight and curved shafts as well as fluted shafts are known. Representative of these known hip prostheses are those described in the following: U.S. Pat. No. 4,279,042—T. P. Andriacchi, et al; U.S. Pat. No. 3,965,490—I. P. Murray, et al; U.K. Patent Application, G.B. No. 2,069,340A—K. Hardinge. Known commercial products include the Bard Contour TM and Link SP-femoral hip prosthesis, manufactured by Waldemar Link Hamburg, West Germany and the Isoelastique Butel hip prosthesis by Butel, Grenoble, France.

Prosthetic devices provided with porous surfaces for bone ingrowth are also known, e.g. U.S. Pat. No. 3,906,440—W. Rostoker, et al and British Pat. Spec. No. 1,554,454—J. C. Bokros.

Nevertheless, further improvements in the total design of hip prosthesis are required to assure stable fixation of the implanted prosthesis at the bone/metal interface. Thus, in cemented prosthetic devices there has not been satisfactory fixation due to the various stress loads, i.e. compression, shear and torsion, to which the implanted device is subjected. These mechanical forces, especially shear and torsion, weaken the bone cement bond. In addition, it is known that there is a tendency for bone resorption which also weakens the cement bond between the bone, e.g. intramedullary canal of the femur, and the femoral prosthesis.

On the other hand, by providing a bone ingrowth surface on the prosthetic device a more stable fixation would be expected and some advances along these lines have been made. However, experiments by the present inventors have shown that bone ingrowth requires the prosthesis to be stably fixed without movement for at least six weeks and any relative motion of the prosthesis during that period prevents or minimizes bony ingrowth.

As a result, an incidence of ten to twenty percent of femoral stem loosening or failure in total hip arthroplasty patients followed over 5 or more years, especially in younger patients, has been reported.

SUMMARY OF THE INVENTION

Accordingly, it is an object of this invention to provide a femoral hip prosthesis which avoids these problems of prior art devices.

A particular object of the invention is to provide a femoral hip prosthesis which combines long term stabilization by bone ingrowth proximally with initial stable fixation distally.

A further object of the invention is to provide a hip prosthesis which closely approximates in geometry and curvature the natural femur, including a curved long stem or shaft having a fluted design in the distal portion, to obtain maximum torque resistance, which is wide in the medial-lateral direction and curved medially in the proximal portion to maximize bone-prosthesis contact area, and which has a bone ingrowth media on both the anterior and posterior aspects in the proximal portion of the shaft.

A still further object of the invention is to provide a femoral hip prosthesis in which the femoral head and neck are anteverted from the collar at about 10°, and at an angle with respect to the shaft of the prostheses of about 135°, and wherein the collar extends medially from the prosthesis to allow load (stress) sharing and distribution with the bone to an extent of about 30% of the total load, with the remaining 70% being borne by the shaft (stem).

Generally speaking, these and other objects of the invention, which will become evident from the following more detailed description and specific embodiments, are accomplished by a femoral insert for hip joint prosthesis having a spherical shaped head member, a neck member connected to the head member and terminating at a collar, and a shaft member connected at its proximal end to the collar and including a proximal portion and a distal portion. The proximal portion has a cross-section which is rectangular at the proximal end at the collar and gradually tapers to a relatively constant square cross-section. The distal portion of the shaft member or stem has the configuration of and functions as an intramedullary rod, for example, a generally circular cross-section which is curved to match the anterior bow of the femur. The upper half of the proximal portion is wide in the medial-lateral direction with flat anterior and posterior sides, is curved medially, and may be straight or curved in the lateral aspect. The lower half of the proximal portion is straight in the medial and lateral aspects as well as in the anterior and posterior sides. A porous bone ingrowth surface, such as sintered titanium metal, is provided on at least one of the proximal anterior and proximal posterior sides. The collar is flush with the anterior and posterior sides and extends medially. Accordingly, firm fixation of the prosthesis is initially provided by the distal intramedullary rod portion while long term stabilization is achieved proximally through the bony ingrowth surface.

The neck member may be anteverted with respect to the collar at an angle of about 10° to about 20° and may be at an angle to the longitudinal axis through the proximal portion of the shaft of about 125° to about 140°. The curved distal portion of the shaft is also preferably fluted.

In one embodiment, the lateral aspect of the shaft is straight in the entire proximal portion. In an alternative embodiment, the upper portion of the lateral aspect is curved over about the same or shorter length as the medial curve but with a slightly smaller radius of curvature. In this embodiment, the curved upper portion of the lateral aspect includes an upstanding curved rib which extends from the underside of the collar and terminates tangentially into the body of the lateral aspect.

BRIEF DESCRIPTION OF THE DRAWINGS

The invention will now be described in greater detail with respect to specific embodiments thereof with the aid of the accompanying drawings in which:

FIG. 1 is a front elevation view of an embodiment of the prosthetic device of the invention shown installed within the intramedullary of a left femur;

FIG. 2 is a side elevation view of the left leg prosthetic device of FIG. 1;

FIG. 3 is a top view of the left leg prosthetic device of FIG. 1;

FIG. 4 is a front elevation view similar to FIG. 1 of a right leg prosthetic device according to the invention;

FIG. 5 is a side elevation view of the right leg prosthetic device of FIG. 4;

FIG. 6 is a top view of the right leg prosthetic device of FIG. 4;

FIG. 7 is a section view in the direction of line 7—7 of FIG. 4.

FIG. 8 is a section view in the direction of line 8—8 of FIG. 4;

FIG. 9 is a section view in the direction of line 9—9 of FIG. 4;

FIG. 10 is a partial side elevation view of an alternative embodiment of a left leg prosthetic device according to the invention.

FIG. 11 is a view, partially in section, in the direction of line 11—11 of FIG. 10; and FIG. 12 is a section view in the direction of line 12—12 of FIG. 11.

DETAILED DESCRIPTION OF THE INVENTION

Firm implantation of the femoral, insert prosthetic device of this invention is provided by combining a unique configuration of the component parts, namely spherical head, neck, collar, and shaft which closely approximate the natural configuration of the normal femoral shaft, femoral neck and head, and specifically an anteverted femoral neck, with a shaft which, in the proximal portion, is wide in the medial-lateral direction, at least partially straight in the lateral direction and curved in the medial direction to match the inside contour of the femoral shaft and in the distal portion is fabricated to the configuration of an intramedullary rod, preferably it is curved to match the anterior bow of the femur. Opposite curvatures are provided for each of the left and right leg femoral prostheses.

In addition, at least one of, and preferably both, the anterior and posterior aspects are provided with a bone ingrowth surface and, therefore, the need for cement fixation, which is one of the major causes of total hip failure, is eliminated.

Accordingly, firm fixation is achieved in the greater trochanter region by making the upper segment (proximal end) of the shaft broad in the medial-lateral direction. The bone ingrowth surfaces on the anterior and/or posterior aspects provide still further fixation of the proximal portion of the shaft while the intramedullary rod portion of the shaft at the distal end is firmly fixed by virtue of its being curved to stimulate the anatomical configuration of the normal femur. The initial stable fixation of the distal intramedullary rod portion of the shaft in the intramedullar of the femoral shaft permits bone ingrowth to occur proximally to provide an overall secure fit of the entire prosthesis without requiring any adhesive cement.

Turning now to to the drawings, a left femoral prosthesis is shown generally at 1 in FIGS. 1-3. The prosthetic device includes spherical head member 2, neck member 3, collar 4 and shaft member 5. The prosthetic device is preferably fabricated from titanium metal or titanium alloy, but any other biologically compatible, inert metal that has sufficient mechanical strength can be used.

FIGS. 4, 5 and 6 are similar to FIGS. 1, 2 and 3, respectively, but are for a right femoral prosthesis. In FIGS. 4-9, the spherical head member, neck member, collar and shaft member are designated by 42, 43, 44 and 45, respectively.

As will be described in greater detail below, the direction of angulation of the neck member and the direction of the curved bow of the distal stem portion are in one direction for the left femoral prosthesis and in the opposite direction for the right femoral prosthesis. However, the right and left femoral prostheses are otherwise constructed in the same manner and are, generally speaking, mirror images of each other.

Head member 2, 42 is generally globular in shape and assumes somewhat more than a hemisphere. The head member has a highly polished bearing surface to mate with the hip socket, which may be the natural hip socket or an artifical prosthesis in the case of total hip replacement. The femoral head member has a diameter of about 28 millimeters, although smaller and larger sizes can be stocked or prepared as needed for individual patients.

The underside 52 of head member 42 is substantially flat (FIG. 7), although it can also be slightly curved, either convexly or concavely, to where the neck member joins the underside in substantially the center portion thereof.

The neck member which connects the head member to the shaft at the collar, is generally rectangular in cross-section and is broader in the inferior and superior direction than in the anterior and posterior direction. The base of the neck at the collar is broader than its apex where it joins the head to approximate the pyrimidal configuration of a normal femoral neck. Additional structural strength is provided by having the base and the apex diverge outwardly at the juncture with the collar and head member, respectively.

As best seen in FIG. 2, the longitudinal axis 13 of neck 3, intersects the longitudinal axis 15, of shaft 5 at an angle $\alpha$ in the range of 125° to 140°, preferably about 135°. The neck member is also anteverted with respect to the collar by the angle $\beta$, between longitudinal axis 13 and line 14 which is an extension of longitudinal axis 15 of shaft member 5 through the upper proximal portion thereof, which ranges from about 10° to about 20°, preferably about 10° to 12°, especially about 10°. As seen in FIG. 3, line 14 is parallel to and equidistant from the anterior and posterior edges of collar 4.

Collar 4, 44, extends medially from the shaft member at extension 16, 56 but is otherwise flush with the lateral sides of the shaft member. As seen in FIG. 7, extension 56 has an arcuate elliptical periphery 59 which bulges slightly from either of the anterior 57 and posterior 48 lateral sides of shaft member 45. The extended collar rests on the upper surface of the femoral shaft bone (as shown in phantom outline in FIG. 1 and FIG. 2) to provide for medial load transfer and stabilization of the implanted prosthesis.

The upper proximal portion 6 of shaft member 5 is broad in the medial-lateral direction with the greatest width occurring at the juncture with collar 4 and gradually tapering to a substantially constant width at or near the midpoint thereof. In the widened upper medial-lateral region of the upper proximal portion bone ingrowth pads 20 and 60, 61 are provided on the anterior and posterior lateral sides, respectively. These are preferably formed from sintered titanium metal of 300-400 microns pore size, although any other bone ingrowth media or construction can be used. Preferably, as shown in FIG. 7, the bone ingrowth pads are securely fitted within the notched undercut portions 62, 63 in the anterior and posterior lateral faces 57, 58, respectively. The outer surfaces of the bone ingrowth pads are preferably flush with the lateral sides 17, 18 and 57, 58, respectively. The configuration of the bone ingrowth pads is not particularly critical but generally they will be in the same general configuration as the lateral sides and should cover the majority of the surface area of the upper portion, for example, about 50 to about 90%, of the area of the upper portion, or about 1 to 3 square inches for each pad.

The upper proximal portion has a straight lateral aspect 26 and is slightly curved in the upper half of the medial aspect 24 to match the inside contour of the femoral shaft thereby allowing for firm fixation in the greater trochanteric region. The curve of the upper medial aspect makes a smooth transition with the lower flat medial aspect which is substantially parallel to the straight lateral aspect.

The lower distal portion 7 of shaft member 5 is curved to match the anterior bow of the femur and is fluted over its entire length which is about one-half of the total length of the shaft member from collar 4 to the free end 31. The curved/fluted configuration enables the distal portion to function as an intramedullary rod to again provide firm fixation of the prosthesis in the femoral shaft at the distal end so that bone ingrowth can proceed at the proximal end.

As can be seen from FIGS. 1 and 4, the curve of the distal portion of the shaft is in the opposite direction than the direction of anteversion of neck member 3, 43. This can also be seen in FIGS. 3 and 6 where the free end 31, 71 of the shaft member is "behind" collar 4, 44 or into the plane of the paper while neck member 3, 43 and head member 2, 42 are "in front of" collar 4, 44 or out of the plane of the paper. In other words, the right hip prosthesis and left hip prosthesis are mirror images of each other.

As seen in FIG. 8, the lower half of the upper proximal portion 46 of shaft member 45 has a substantially square cross-section with slightly rounded corners. The upper half of the upper proximal portion which includes the curved medial aspect 64 has a rectangular cross-section (FIG. 7). The fluted distal portion 47 has a substantially circular cruciform cross-section (FIG. 9). Flutes 8, 48 are circumferentially spaced at 90° intervals around the distal portion 7, 47 and their edges merge smoothly into the rounded ribs 9, 49 which separate them and which are circumscribed within a circle having a diameter which is substantially equal to the length of a side of the square cross-section of the upper proximal portion 6, 46, i.e. the distance between the medial and lateral aspects and between the anterior and posterior sides. The width and depth of each of the four flutes is substantially constant along the length of the distal portion.

FIGS. 10, 11 and 12 illustrate a slightly modified embodiment of a hip prosthesis (illustrated for the left hip only) according to the invention.

In this embodiment, the lateral aspect 126 in the upper region 135 of the upper proximal portion 106 is also curved but with a somewhat smaller radius of curvature than the radius of curvature for the curved medial aspect 124. Curved rib 138 is provided in the central portion of the upper region 135 beginning at the underside of collar 104 and terminating in the lateral aspect at or near the transition from the curved upper region 135 to the straight lower region 136 of lateral aspect 126. As seen in FIGS. 10 and 11, rib 138 blends smoothly and tangentially into the lateral aspect. By appropriate reaming of the greater trochanteric region of the femur additional contact area can be provided between the prosthesis and the femur at the rib 138. Also in this embodiment the extension 116 on collar 104 has a more rounded configuration than the elliptical configuration of extension 16 and does not bulge beyond the lateral walls.

It is envisioned that the hip prosthesis can be stocked in several standard sizes and combinations. For example, the femoral neck can be stocked in lengths l of 28 mm, 30 mm, 34 mm and 40 mm, measured from the base of the collar to the center of the femoral head. Standard sizes for the length L of the shaft member, measured from the base of the collar to the free end, would typically be 200 mm, 220 mm, 230 mm, 250 mm, 260 mm and 270 mm.

For a typical embodiment of the right and left femoral inserts illustrated in FIGS. 1-9 with a 28 mm diameter spherical head the neck member will be about 34 mm in length, the overall length of the collar LC will be about 42 mm, the width W is about 15 mm, the length L is about 230 mm and the length of the fluted distal portion is about 125 mm.

Accordingly, the hip prosthesis of the present invention will have the following advantages:

1. Allows early weight bearing, such as in conventional total hip arthoplasty, but not present ingrowth systems;
2. Avoids use of cement;
3. Ideal for young patients, need not enlarge acetabulum in contrast to resurfacing arthoplasty;
4. Does not require any unconventional surgical procedures since orthopaedic surgeons are familiar with reaming the intramedullary canal;
5. Reduces loosening by a combination of proximal bony ingrowth and distal fixation.

What is claimed is:

1. In a femoral insert for hip joint prosthesis having a spherical shaped head member, a neck member connected to the head member and terminating at a collar, and a shaft member having a proximal portion connected to the collar and extending approximately half the extent of the shaft member, and a distal portion extending therefrom, the improvement comprising
the collar being flush to the anterior and posterior sides of and extending medially from the shaft member;
the proximal portion having a longitudinal axis and a substantially straight lateral aspect, an upper half which is broad in the medial-lateral direction and curved in the medial aspect and having a generally rectangular cross-section which is widest at the collar and gradually tapers to a generally square cross-section, and a lower half which has flat sides and a generally square cross-section of the upper half;

said neck member being anteverted with respect to the collar and proximal portion at an angle of about 10° to 20° and is at angle to said longitudinal axis through said proximal portion of said shaft member of about 125° to about 140°;

at least one of the anterior and posterior sides of the upper half of said proximal portion including at least one porous bony ingrowth surface; and said distal portion having the curved configuration of an intramedullary rod and curving in the opposite direction from the direction of said anteversion of said neck member, and said proximal portion extending straight in a plane parallel to said lateral aspect, whereby firm fixation of the prosthesis is initially provided by the distal intramedullary rod portion while long term stabilization is achieved proximally through the bony ingrowth surface.

2. The femoral insert of claim 1 wherein the distal portion has a generally circular cross-section.

3. The femoral insert of claim 1 or 2 wherein the distal portion is curved to match the anterior bow of the femur.

4. The femoral insert of claim 3 wherein the distal portion is fluted.

5. The femoral insert of claim 1 or 2 wherein the distal portion is fluted.

6. The femoral insert of claim 1 wherein the angle $\beta$ is about 10° and the angle $\alpha$ is about 135°.

7. The femoral insert of claim 1 wherein said straight lateral aspect extends in both the upper and lower halves of the proximal portion.

8. The femoral insert of claim 1 wherein the medial aspect is curved in the upper half of the proximal portion and is flat in the lower half of the proximal portion.

9. The femoral insert of claim 5 in which the upper half of the lateral aspect further comprises an upstanding curved rib which extends from the underside of the collar and terminates tangentially into the body of the lateral aspect.

10. The femoral insert of claim 1 or claim 6 which comprises porous bone ingrowth surfaces on both the posterior and lateral sides comprising a coating of a sintered titanium metal or alloy having a pore size in the range of 300 to 400 microns.

11. A femoral insert for hip joint prosthesis which comprises a spherical shaped head member, a neck member connected to the head member and terminating at a collar, a long stem member having a proximal portion connected to the collar and extending approximately half the extent of the shaft member, and a distal portion extending therefrom and having the curved configuration of an intramedullary rod and being curved to match the anterior bow of the femur, the proximal portion of said long stem having an upper half which is broad in the medial-lateral direction and curved in the medial aspect to match the inside contour of the femoral shaft and having a generally rectangular cross-section which is widest at the collar and gradually tapers to a generally square cross-section, said proximal portion having a longitudinal axis being straight in the anterior and posterior aspects, and a lower half which has flat sides and substantially the same generally square cross-section as that of the upper half, said neck member being anteverted with respect to the collar and proximal portion at an angle $\beta$ of about 10° to 20°, said distal portion of said stem member being curved in a direction opposite to the direction of said anteversion of said neck member, said long stem member having a length of at least about 200 mm and sufficient to extend to the intramedullary canal, said neck member forming an angle to said longitudinal axis through the proximal portion of the stem member of about 125° to about 140°, and porous bone ingrowth surfaces on both the posterior and lateral sides of the upper half of the proximal portion of the stem member, whereby firm fixation of the prosthesis is initially provided distally by the long curved stem and proximally by the broad upper half of the proximal portion of the stem member fitting tightly in the reamed out portion of the femoral canal, including bone-prosthesis contact area at the curved medial aspect and long term stabilization is achieved proximally through the growth of bone into the bony ingrowth surfaces.

12. The femoral insert of claim 11 wherein the distal portion has a generally circular cross-section and is fluted, and said porous bone ingrowth surfaces comprise a coating of a sintered titanium metal or alloy having a pore size in the range of 300 to 400 microns.

* * * * *

UNITED STATES PATENT AND TRADEMARK OFFICE
CERTIFICATE OF CORRECTION

PATENT NO. : 4,546,501

DATED : October 15, 1985

INVENTOR(S) : RAMON B. GUSTILO, ET AL.

It is certified that error appears in the above-identified patent and that said Letters Patent is hereby corrected as shown below:

Claim 10, line 1, (column 7, line 46), delete "or claim 6".

Signed and Sealed this

Seventh Day of January 1986

[SEAL]

Attest:

DONALD J. QUIGG

Attesting Officer

Commissioner of Patents and Trademarks